United States Patent [19]

Stanton

[11] 4,390,700
[45] Jun. 28, 1983

[54] 1-CARBOXYAZAALKANOYL-TETRAHYDROQUINOLINE-2-CARBOXYLIC ACIDS

[75] Inventor: James L. Stanton, Ossining, N.Y.

[73] Assignee: Ciba-Geigy Corporation, Ardsley, N.Y.

[21] Appl. No.: 205,804

[22] Filed: Nov. 10, 1980

[51] Int. Cl.³ .................. C07D 215/12; C07D 215/16
[52] U.S. Cl. .................................... 546/165; 424/258
[58] Field of Search ............................... 546/165, 156

[56] References Cited

U.S. PATENT DOCUMENTS 4,128,653  12/1978  Cushman et al. ................... 546/226

FOREIGN PATENT DOCUMENTS 12401    6/1980  European Pat. Off.
3004370  8/1980  Fed. Rep. of Germany

OTHER PUBLICATIONS

Zecchini et al., "J. Heterocyclic Chemistry," 16, 1589 (1979).

Primary Examiner—Donald G. Daus
Assistant Examiner—D. B. Springer
Attorney, Agent, or Firm—Norbert Gruenfeld

[57] ABSTRACT

1-(Carboxy-azaalkanoyl or azaaralkanoyl)-1,2,3,4-tetrahydroquinoline-2-carboxylic acids, e.g., those of the formula

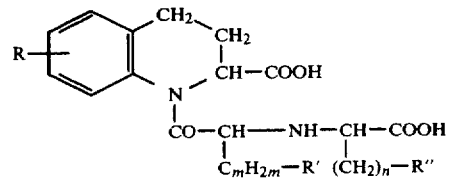

R = H, alkyl, alkoxy, halogeno or $CF_3$;
R' = H or amino;
R" = H or R—phenyl;
m = 1 to 4;
n = 1 to 3 and functional derivatives thereof, are antihypertensive and cardioactive agents.

5 Claims, No Drawings

1-CARBOXYAZAALKANOYL-TETRAHYDROQUINOLINE-2-CARBOXYLIC ACIDS

BACKGROUND OF THE INVENTION

"Peptides containing 1,2,3,4-tetrahydroquinoline-2-carboxylic acids" are described by G. P. Zecchini et al in J. Heterocyclic Chem. 16, 1589 (1979), for the cyclization with acetic anhydride, to form "1H,3H,5H-oxazolo[3,4-a]quinolin-3-one derivatives". Also, 1-(mercapto- or acylthioalkanoyl)-1,2,3,4-tetrahydroquinoline-2-carboxylic acids, and salts thereof, are known, e.g., according to DOS No. 3,004,370, as possessing antihypertensive activity. Surprisingly it was found that either by introduction of another aminoacid moiety into the former mono-peptides, or by exchange of the latter mercaptoalkanoyl moiety by a dipeptide chain, superior antihypertensive agents are obtained.

SUMMARY OF THE DISCLOSURE

The present invention concerns and has for its object the provision of new 1-(carboxy-azaalkanoyl or azaaralkanoyl)-1,2,3,4-tetrahydroquinoline-2-carboxylic acids, more particularly of those corresponding to Formula I:

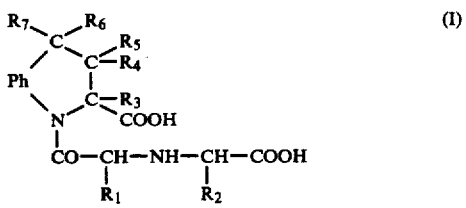

wherein Ph is unsubstituted 1,2-phenylene, or 1,2-phenylene substituted by one to three identical or different members selected from lower alkyl, lower alkoxy, lower alkylenedioxy, hydroxy, halogeno and trifluoromethyl; $R_1$ is hydrogen, lower alkyl or aminoalkyl; $R_2$ is lower alkyl or HPh-lower alkyl; and each of $R_3$, $R_4$, $R_5$, $R_6$ and $R_7$ is hydrogen or lower alkyl; the amides, mono- or di-lower alkylamides, lower alkyl esters, (amino, mono- or di-lower alkylamino, carboxy or lower carbalkoxy)-lower alkyl esters, or pharmaceutically acceptable salts thereof; as well as of corresponding pharmaceutical compositions and of methods for the preparation and application of said products, which are useful antihypertensive and cardioactive agents.

DESCRIPTION OF THE PREFERRED EMBODIMENTS

The 1,2-phenylene group Ph and/or the phenyl group HPh, are preferably unsubstituted or monosubstituted, and their substituents are illustrated by the following groups; lower alkyl, e.g., methyl, ethyl, n- or i-propyl or -butyl; lower alkoxy, e.g., methoxy, ethoxy, n- or i-propoxy or -butoxy; lower alkylenedioxy, e.g., methylenedioxy, 1,1- or 1,2-ethylenedioxy; hydroxy; halogeno, e.g., fluoro, chloro or bromo; or trifluoromethyl.

A lower alkyl group $R_1$ and/or $R_2$ is preferably methyl, ethyl, n- or i-propyl or -butyl; the aminoalkyl group $R_1$ is preferably ω-amino-(ethyl, propyl, butyl or pentyl); and the aralkyl group $R_2$ is also preferably ω-HPh-(methyl, ethyl or propyl).

Each of $R_3$, $R_4$, $R_5$, $R_6$ and $R_7$ is preferably hydrogen, but also lower alkyl, advantageously methyl, or another of those mentioned previously.

The term "lower", referred to above and hereinafter in connection with organic radicals or compounds respectively, defines such with up to 7, preferably up to 4, and advantageously but one or two carbon atoms.

Said functional derivatives, wherein either one or both carboxy groups are esterified or amidized, are preferably the mono- or bis-lower alkyl esters, e.g. the methyl, ethyl, n- or i-propyl or -butyl esters; the mono- or bis-amide, or the correspondingly N-alkylated amides, e.g. mono- or dimethylamide, or said substituted lower alkyl esters, preferably the half-esters with a free 1,2,3,4-tetrahydroquinoline-2-carboxy group, e.g. the ω-(amino, mono- or dimethylamino, carboxy or carbethoxy)-(ethyl, propyl or butyl)esters.

Pharmaceutically acceptable salts are preferably metal or ammonium salts of said acids, more particularly alkali or alkaline earth metal salts, e.g., the sodium, potassium, magnesium or calcium salt; or advantageously easily crystallizing ammonium salts derived from ammonia or organic amines, such as mono-, di- or tri-lower(alkyl, cycloalkyl or hydroxyalkyl)-amines, lower alkylenediamines or lower(hydroxyalkyl or aralkyl)-alkylammonium bases, e.g., methylamine, diethylamine, triethylamine, dicyclohexylamine, triethanolamine, ethylenediamine, tris(hydroxymethyl)-aminomethane or benzyl-trimethylammonium hydroxide. Said amphoteric compounds of Formula I form also acid addition salts, which are preferably such of therapeutically acceptable inorganic or organic acids, such as strong metalloidic acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, ethylenesulfonic, halogenbenzenesulfonic, toluenesulfonic, naphthalenesulfonic, sulfanilic or cyclohexylsulfamic acid.

The compounds of this invention exhibit valuable pharmacological properties, primarily hypotensive, antihypertensive and cardioactive effects, inter alia due to their angiotensin converting enzyme inhibitory activity. This is demonstrable by in vivo or in vitro animal tests, using advantageously mammals, e.g., rats, cats, dogs or isolated organs thereof, as test objects. The animals may either be normotensive or hypertensive e.g., genetically hypertensive rats, or renal hypertensive rats and dogs, and sodium-depleted dogs. Said compounds can be applied to them enterally or parenterally, advantageously orally or intravenously, for example within gelatin capsules or in the form of starchy suspensions or aqueous solutions respectively. The applied dosage may range between about 0.01 and 50 mg/kg/day, preferably between about 0.1 and 25 mg/kg/day, advantageously between about 1 and 10 mg/kg/day.

The in vivo lowering effect on the blood pressure is recorded either directly by means of a catheter, for example placed in the dog's femoral artery, or indirectly by sphygmomanometry at the rat's tail, and a transducer, expressing the blood pressure prior and after dosing in mm Hg. Thus, for example, the representative members of the compounds of this invention, illustrated by the Examples herein, are very effective in hypertensive rats and dogs at p.o.-doses as low or lower than 10 mg/kg/day.

They also exhibit an inhibitory effect against the angiotensin I pressure response of normotensive rats. The enzyme renin, normally causes specific hydrolysis of the circulating protein renin-substrate. This hydrolysis generates angiotensin I, which is further hydrolyzed by the action of said converting enzyme to the potent vasoconstrictor angiotensin II. The inhibition of said enzyme prevents the generation of angiotensin II from I and, therefore, attenuates any pressure response following an angiotensin I challenge.

The corresponding in vivo test is performed with male, normotensive rats, which are anesthetized with 100-120 mg/kg i.p. of sodium ethyl-(1-methylpropyl)-malonylthionrea. A femoral artery and saphenous vein are cannulated for direct blood pressure measurement and i.v. administration of angiotensin I and compounds of this invention. After the basal blood pressure is stabilized, pressor responses to 3 challenges of 0.33 μg/kg of angiotensin I i.v., in 5 minute intervals, are obtained. Such pressure responses are again obtained, 5, 10, 15, 30 and 60 minutes after either i.v., or p.o. administration (stomach tube) of the compounds to be tested, and compared with the initial responses. Any observed decrease of said pressor response is an indication of angiotensin I converting enzyme inhibition, ranging up to 80% after 10 mg/kg i.v., or 50 mg/kg p.o. doses, which decrease may be sustained up to 60 minutes.

The in vitro inhibition of the angiotensin-converting enzyme by the compounds of this invention can be demonstrated analogous to Biochem. Biophys. Acta 293, 451 (1973). According to this method said compounds are dissolved at about 1 mM concentrations in phosphate buffer, externally cooled with ice. To these solutions various μl amounts of 1 mM of histidyl-leucine in phosphate buffer are added, followed by 100 μl of 5 mM hippuryl-histidyl-leucine in phosphate buffer and 50 μl of the angiotensin-converting enzyme, which is freshly prepared from lungs of adult male rabbits in Tris buffer, containing potassium and magnesium chloride, as well as sucrose. Said solutions are incubated at 37° for 30 minutes and combined with 0.75 ml of 0.6 N aqueous sodium hydroxide to stop further reaction. Then 100 μl of o-phthalaldehyde are added at room temperature, and 10 minutes later 100 μl of 6 N hydrochloric acid. These samples are read against water in a spectrophotometer set at 360 nm, and the optical densities thereof estimated. They are corrected for the standard curve via a conversion factor expressing nanomoles of histidyl-leucine formed during said 30 minute incubation period. The results are plotted against drug concentration to determine the $IC_{50}$, i.e., the drug concentration which gives half the activity of the control sample containing no drug. Again, said representative members of the compounds of this invention are very effective in this in vitro test system, down to $IC_{50}$ values as low or lower than 6 nM.

Accordingly, the compounds of this invention are valuable antihypertensive agents, especially useful for ameliorating hypertension (regardless of etiology) and/or heart-conditions, such as congestive heart failure, and/or other edemic or ascitic diseases, e.g. hepatic cirrhosis. They are also useful intermediates in the preparation of other valuable products, especially of corresponding pharmaceutical compositions.

Particularly useful for said purpose are those compounds of Formula I, wherein Ph is unsubstituted 1,2-phenylene, or 1,2-phenylene substituted by one or two identical or different members selected from lower alkyl, lower alkoxy, hydroxy and halogeno, or 1,2-phenylene substituted by one lower alkylenedioxy or trifluoromethyl group; $R_1$ is hydrogen, lower alkyl or ω-amino-lower alkyl; $R_2$ is lower alkyl or ω-HPh-lower alkyl; and each of $R_3$, $R_4$, $R_5$, $R_6$ and $R_5$ is hydrogen or lower alkyl; the amides, mono- or di-lower alkylamides, lower alkyl esters, (amino, mono- or di-lower alkylamino, carboxy or lower carbalkoxy)-lower alkyl esters, or pharmaceutically acceptable alkali metal, alkaline earth metal, ammonium or acid addition salts thereof.

More preferred are those compounds of Formula I, wherein Ph is 1,2-phenylene, unsubstituted or mono-substituted by lower alkyl, lower alkoxy, lower alkylenedioxy, hydroxy, halogeno or trifluoromethyl; $R_1$ is lower alkyl or ω-amino-lower alkyl; $R_2$ is lower alkyl or ω-HPh-lower alkyl; and each of $R_3$, $R_4$, $R_5$, $R_6$ and $R_7$ is hydrogen or methyl; or said amides, esters and salts listed in the previous paragraph.

Especially valuable compounds of this invention are those of Formula II

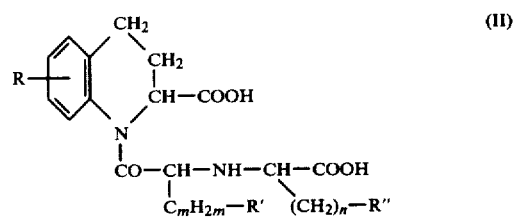

more specifically the tetrahydroquininoline-2S-chiral epimers thereof, wherein R is hydrogen, alkyl or alkoxy with up to 4 carbon atoms, hydroxy, halogeno or trifluoromethyl; preferably in the 6-position; m is an integer from 1 to 4; n is an integer from 1 to 3; R' is hydrogen or amino; and R" is hydrogen or R-phenyl; the mono- or bis-amide, the mono- or bis-lower (alkyl or ω-aminoalkyl) esters, and pharmaceutically acceptable alkali metal, ammonium or acid addition salts thereof.

The most preferred compounds of this invention are those of Formula II, wherein R is hydrogen, methyl, methoxy, hydroxy or chloro, advantageously in the 6-position, m is the integer 1, n is the integer 2, R' is hydrogen and R" is phenyl, or said amides, esters and salts listed in the preceding paragraph.

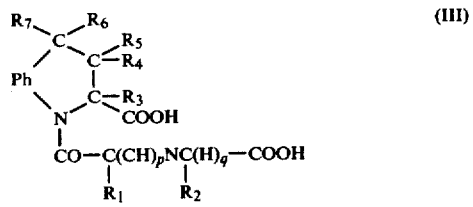

or said functional derivatives thereof, wherein one of the integers p and q is 0 and the other is 1; or (2) condensing a compound of Formula IV

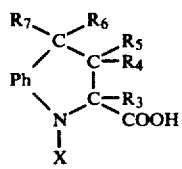

or said functional derivatives thereof, with a reactive functional derivative of a compound of Formula V

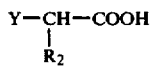

wherein X is hydrogen and Y is HOCO—CH-$R_1$—N—COOR$_o$, in which R$_o$ is t-butyl or benzyl; or X is CO—CHR$_1$—Z and one of Y and Z is amino and the other reactively esterified hydroxy, and converting said COOR$_o$ group into hydrogen; or (3) hydrolysing or alcoholyzing a compound of Formula VI

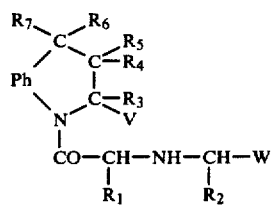

wherein at least one of V and W is cyano, and the other is said free, amidized or esterified carboxy group, and if desired, converting any resulting compound into another compound of this invention.

The hydrogenation of compounds III is performed according to known methods, e.g. either with catalytically activated or nascent hydrogen, such as hydrogen in the presence of platinum, palladium or nickel catalysts, or generated electrolytically, or by the action of metals on acids or alcohols. Preferred is the asymmetric hydrogenation with chiral catalysts, as, for example, prepared from a rhodium salt with (R)-1,2-bis-(diphenylphosphino)-propane or (R)-1,2-bis(o-anisyl-phenylphosphino)-ethane and 1,5-cyclooctadiene. Also reducing agents may be used, such as simple or complex light metal hydrides, e.g., boranes, or advantageously alkali metal borohydrides or cyanoborohydrides. Said compounds III are advantageously formed in situ, i.e., from the corresponding amines and aldehydes or ketones respectively, which are either known, or prepared analogous to processes 2 or 3.

Reactive functional derivatives of compounds V are preferably ester-halides, simple or mixed anhydrides, such as the lower alkyl half esters of said acid chlorides, the cyclic anhydride, or mixed acetic or cyanoacetic anhydrides. A reactively esterified hydroxy group Y or Z, is preferably halogeno, e.g., chloro, bromo or iodo; or aromatic sulfonyloxy, e.g., tosyloxy or brosyloxy. Said condensation of compounds IV and V occurs either spontaneously, or in the presence of condensing agents, such as organic or inorganic bases, e.g. said salt-forming amines or alkali metal carbonates, or disubstituted carbodiimides. Any resulting compound containing the aza-protecting group COOR$_o$, can be deprotected according to methods well known in peptide chemistry, advantageously by catalytic hydrogenation as shown above, or hydrolysis as shown below. Said starting materials are also known, or if new, may be prepared according to an analogous condensation step 2.

The hydrolysis of the nitriles VI to the corresponding acids or amides is advantageously carried out with inorganic acids, such as hydrohalic or sulfuric acids, in known manner; and said alcoholysis is analogously performed in the presence of both said acids and the corresponding unsubstituted or substituted lower alkanols. This starting material may also be obtained analogous to process 2, from the known compounds IV with X=H, and the corresponding nitriles V.

The compounds of the invention so obtained, can be converted into each other according to conventional methods. Thus, for example, resulting amides or esters may be further hydrolyzed or alcoholyzed (transesterified) according to process 3), or with aqueous alkalies, such as alkali metal carbonates or hydroxides, respectively. Resulting free acids may be esterified with said unsubstituted or substituted lower alkanols or diazoalkanes, or converted into said metal, ammonium or acid addition salts in conventional manner.

Thus, for example, any resulting free (amphoteric) compound can be converted into a corresponding metal, ammonium or acid addition salt respectively, by reacting it with an equivalent amount of the corresponding base, basic salt, acid or ion exchange preparation, e.g. said acids with alkali metal or ammonium hydroxides or carbonates, or said acids, amides or esters with said inorganic or organic acids respectively. Any resulting salt may also be converted into the free compounds, by liberating the latter with stronger acids or bases respectively, advantageously at the pH-value between about 3 to 5. In view of the close relationship between the free compounds, and the salts thereof, whenever a compound of the invention, or intermediate thereof, is referred to in this context, a corresponding salt is also intended, provided such is possible or appropriate under the circumstances.

In case mixtures of geometrical or optical isomers of the above compounds of Formulae I to VI are obtained, these can be separated into the single isomers by methods in themselves known, e.g., by fractional distillation, crystallization and/or chromatography. Racemic products can likewise be resolved into the optical antipodes, for example, by separation of diastereomeric salts thereof, such as according to J. Org. Chem. 43, 3803 (1978), e.g., by the fractional crystallization of d- or l-(tartrates, mandelates, camphorsulfonates, or 1-napht-hyl-1-ethylisocyanates), or of d- or l-α-methylbenzylammonium, cinchonidine, cinchonine, quinine, quinidine, ephedrine, dehydroabiethylamine, brucine or strychnine)-salts. The preferred starting material of Formula III is the 2-S-optical isomer (epimer) thereof.

The above-mentioned reactions are carried out according to standard methods, in the presence or absence of diluents, preferably such as are inert to the reagents and are solvents thereof, of catalysts, alkaline or acidic condensing or said other agents respectively, for example the standard peptide amino-protecting agents, and/or inert atmospheres, at low temperatures, room temperature or elevated temperatures, preferably at the boiling point of the solvents used, at atmospheric or superatmospheric pressure.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials and reagents should be used in said processes, that lead to the formation of those compounds indicated above as being especially valuable, e.g., those of Formula II, and being the following chiral isomers:

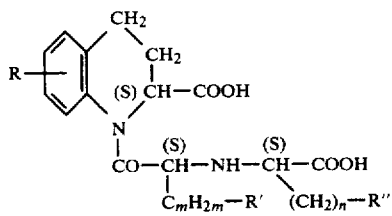

The pharmacologically active compounds of the invention are useful in the manufacture of pharmaceutical compositions comprising an effective amount thereof in conjunction or admixture with excipients suitable for either enteral or parenteral administration. Preferred are tablets and gelatin capsules comprising the active ingredient together with (a) diluents, e.g., lactose, dextrose, sucrose, mannitol, sorbitol, cellulose and/or glycine, (b) lubricants, e.g., silica, talcum, stearic acid, its magnesium or calcium salt and/or polyethyleneglycol, for tablets also (c) binders, e.g., magnesium aluminum silicate, starch paste, gelatin, tragacanth, methylcellulose, sodium carboxymethylcellulose and/or polyvinylpyrrolidone, if desired, (d) disintegrants, e.g., starches, agar, alginic acid or its sodium salt, or effervescent mixtures and/or (e) absorbents, colorants, flavors and sweeteners. Injectable compositions are preferably aqueous isotonic solutions or suspensions; and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances, e.g., other antihypertensive and/or diuretic agents. Said compositions are prepared according to conventional mixing, granulating or coating methods respectively, and contain about 0.1 to 75%, preferably about 1 to 50% of the active ingredient. A unit dosage for a mammal of aout 50-70 kg weight may contain between about 5 and 100 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 to 100 mmHg.

EXAMPLE 1

The mixture of 0.40 g of 1-(S-alanyl)-1,2,3,4-tetrahydroquinoline-2S-carboxylic acid, 0.66 g of ethyl 4-phenyl-2-oxobutanoate, 0.47 g of triethylamine, 0.3 g of Raney-nickel, 1.5 g of 3A molecular sieves and 20 ml of ethanol, is hydrogenated at room temperature and 2.7 atm. for 18 hours. It is filtered, evaporated, the residue partitioned between 15 ml of ethyl acetate and 30 ml of water, the mixture adjusted with 2 N sodium hydroxide to the pH=8.6, the aqueous phase separated and washed with 10 ml of ethyl acetate. It is acidified with 4 N hydrochloric acid to the pH=4.25, extracted thrice with 10 ml of ethyl acetate each, the combined extract dried and evaporated, to yield the 1-[N-(1-carboxyethoxy-3-phenylpropyl)-S-alanyl]-1,2,3,4-tetrahydroquinoline-2S-carboxylic acid of Formula II, with $R = R' = H$, $R'' = C_6H_5$, $m = 1$ and $n = 2$.

It is dissolved in 3 ml of diethyl ether and anhydrous hydrogen chloride is bubbled through the solution. The precipitate formed is filtered off, washed with diethyl ether and dried, to yield the corresponding hydrochloride melting at 95°-100°.

The starting material is prepared as follows: The mixture of 0.80 g of 1-(N-benzyloxycarbonyl-S-alanyl)-1,2,3,4-tetrahydroquinoline-2S-carboxylic acid (J. Heterocyclic Chem. 16, 1592), 0.10 g of 10% palladium-on-carbon and 20 ml of 90% aqueous ethanol is hydrogenated at room temperature and atmospheric pressure for 2 hours. It is filtered, evaporated and the residue triturated with 2 ml of diethyl ether, to yield the 1-(S-alanyl)-1,2,3,4-tetrahydroquinoline-2S-carboxylic acid, showing NMR-peaks at 7.85, 7.07, 3.32 and 1.28 ppm (in $D_6$-DMSO).

EXAMPLE 2

Analogous to the methods disclosed herein, the following 1-(carboethoxy-azaaralkanoyl)-1,2,3,4-tetrahydroquinoline-2S-carboxylic acids of Formula II are prepared:

| No. | R | m | R' | n | R'' | NMR-peaks (ppm) |
|---|---|---|---|---|---|---|
| 1 | H | 0 | H | 2 | $C_6H_5$ | 1.15, 3.78, 5.18 |
| 2 | H | 1 | H | 1 | $C_6H_5$ | 1.15, 1.28, 4.15 |
| 3 | 6-$CH_3$ | 1 | H | 2 | $C_6H_5$ | 1.29, 2.55, 5.05 |
| 4 | 6-$OCH_3$ | 1 | H | 2 | $C_6H_5$ | 1.26, 3.72, 5.15 |
| 5 | 6-Cl | 1 | H | 2 | $C_6H_5$ | 7.20, 7.25, 7.65 | as well as the 1-[N-(1-carboethoxy-3-phenylpropyl)-S-alanyl]-6,7-dimethoxy-1,2,3,4-tetrahydroquinoline-2S-carboxylic acid, showing NMR-peaks at 1.28, 3.71 and 5.10 ppm.

EXAMPLE 3

Preparation of 10,000 tablets each containing 5 mg of the active ingredient of Example 1:

| Formula: | |
|---|---|
| 1-[N—(1-carboethoxy-3-phenylpropyl)-S—alanyl]-1,2,3,4-tetrahydroquinoline-2S—carboxylic acid | 50.00 g |
| Lactose | 1,157.00 g |
| Corn starch | 75.00 g |
| Polyethylene glycol 6,000 | 75.00 g |
| Talcum powder | 5.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 4

Preparation of 10,000 capsules each containing 10 mg of the active ingredient of Example 2/2:

| Formula: | |
|---|---|
| 1-[N—(1-carboethoxy-2-phenylethyl)-S—alanyl]-1,2,3,4-tetrahydroquinoline-2S—carboxylic acid | 100.0 g |
| Lactose | 1,800.0 g |
| Talcum powder | 100.0 g |

Procedure

All the powders are passed through a screen with openings of 0.6 mm. Then the drug substance is placed in a suitable mixer and mixed first with the talcum, then with the lactose until homogenous. No. 3 capsules are filled with 200 mg, using a capsule filling machine.

I claim:

1. A compound corresponding to the formula

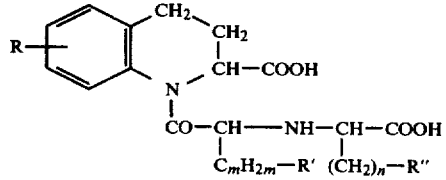

wherein R is hydrogen, alkyl or alkoxy with up to 4 carbon atoms, hydroxy, halogeno or trifluoromethyl; m is an integer from 1 to 4; n is an integer from 1 to 3; R' is hydrogen; and R" is hydrogen or R-phenyl; the mono lower alkyl esters with a free 1,2,3,4-tetrahydroquinoline-2-carboxy group, and pharmaceutically acceptable alkali metal, ammonium or acid addition salts thereof.

2. A compound as claimed in claim 1, in which formula R is hydrogen, methyl, methoxy, hydroxy or chloro; m is the integer 1; n is the integer 2; R' is hydrogen; and R" is phenyl; or said esters and salts listed in claim 1.

3. A compound as claimed in claim 1, wherein R is in the 6-tetrahydroquinoline-position.

4. A compound as claimed in claim 1, in the form of its tetrahydroquinoline-2S-chiral epimer.

5. A compound as claimed in claim 4, and being the 1-[N-(1-carboethoxy-3-phenylpropyl)-S-alanyl]-1,2,3,4-tetrahydroquinoline-2S-carboxylic acid; or a pharmaceutically acceptable metal, ammonium or acid addition salt thereof.

* * * * *